United States Patent
Field

(10) Patent No.: US 9,968,498 B2
(45) Date of Patent: May 15, 2018

(54) DISPOSABLE ABSORBENT VISOR PADS AND METHOD OF USE

(71) Applicant: Christopher Field, West Orange, NJ (US)

(72) Inventor: Christopher Field, West Orange, NJ (US)

(*) Notice: Subject to any disclaimer, the term of this patent is extended or adjusted under 35 U.S.C. 154(b) by 546 days.

(21) Appl. No.: 14/724,540

(22) Filed: May 28, 2015

(65) Prior Publication Data

US 2016/0346140 A1 Dec. 1, 2016

(51) Int. Cl.
| | | |
|---|---|---|
| *A61F 13/15* | (2006.01) | |
| *A61F 13/58* | (2006.01) | |
| *A61F 13/62* | (2006.01) | |
| *A42B 1/18* | (2006.01) | |
| *A42B 3/04* | (2006.01) | |
| *A61F 13/84* | (2006.01) | |
| *A61F 13/47* | (2006.01) | |
| *A42B 3/00* | (2006.01) | |

(52) U.S. Cl.
CPC .............. *A61F 13/58* (2013.01); *A61F 13/47* (2013.01); *A61F 13/622* (2013.01); *A61F 13/84* (2013.01); *A42B 1/18* (2013.01); *A42B 3/003* (2013.01); *A61F 2013/15008* (2013.01)

(58) Field of Classification Search
CPC .. A42B 1/00; A42B 1/06; A42B 1/062; A42B 1/063; A42B 1/18; A42B 1/24; A42B 3/003; A42B 3/22; A61F 13/15; A61F 13/47; A61F 13/58; A61F 13/622; A61F 13/84; A61F 2013/15008
See application file for complete search history.

(56) References Cited

U.S. PATENT DOCUMENTS

| | | | | |
|---|---|---|---|---|
| 2,393,286 A | * | 1/1946 | Brunner | A42B 1/24 2/209.13 |
| 2,416,062 A | * | 2/1947 | Mercer | A42B 1/02 2/175.5 |
| 3,146,462 A | * | 9/1964 | Militello | A42B 3/105 2/205 |
| 4,201,009 A | * | 5/1980 | Burridge, Jr. | A42B 1/006 2/175.1 |
| 4,293,958 A | | 10/1981 | Zauner | |
| 4,345,336 A | * | 8/1982 | Plastino | A42B 3/10 2/171.1 |
| 4,393,519 A | | 7/1983 | Nicastro | |
| 5,003,639 A | * | 4/1991 | White | A42B 1/18 2/195.1 |
| 5,075,898 A | | 12/1991 | Bedient | |
| 5,592,696 A | * | 1/1997 | Oliver | A42B 1/02 2/175.3 |
| 5,659,896 A | * | 8/1997 | Taylor | A61F 9/045 2/12 |

(Continued)

*Primary Examiner* — Kathryn E Ditmer

(74) *Attorney, Agent, or Firm* — Thomas J. Germinario

(57) ABSTRACT

A disposable absorbent pad is removably attachable to the upper surface of the visor of a helmet, hardhat, cap or other headgear. The pads are made in various sizes, shapes and colors to conform to the visors to which they may be applied. Their obverse sides consist of a high-capacity absorbent material, while their reverse sides contain an adhesive strip, for hard visor surfaces, or hook-and-loop strips, for fabric visors. The pads prevent liquid/moisture from dripping off the visor into the face and eyes of the wearer and are disposably replaceable after each use.

3 Claims, 3 Drawing Sheets

(56) References Cited

U.S. PATENT DOCUMENTS

| | | | | |
|---|---|---|---|---|
| 5,701,607 A | * | 12/1997 | Kaiser | A42B 1/062 2/10 |
| 5,887,289 A | * | 3/1999 | Theoret | A42B 1/08 2/195.1 |
| 5,956,773 A | * | 9/1999 | LaMantia | A42B 1/062 2/181 |
| 6,029,272 A | | 2/2000 | Bazin | |
| 6,081,933 A | * | 7/2000 | Partsch, IV | A42B 3/227 2/195.1 |
| 6,173,447 B1 | | 1/2001 | Arnold | |
| 9,179,720 B1 | * | 11/2015 | Bonadio, Jr. | A42B 1/062 |
| 2007/0143906 A1 | * | 6/2007 | Renteria | A42B 1/064 2/195.1 |
| 2010/0277944 A1 | * | 11/2010 | Hurwitz | A41D 27/08 362/570 |
| 2012/0236544 A1 | * | 9/2012 | Dorman | A42B 3/0406 362/106 |
| 2012/0278969 A1 | | 11/2012 | Aronson | |
| 2013/0180025 A1 | * | 7/2013 | Bright | A41D 1/22 2/69 |
| 2013/0180035 A1 | * | 7/2013 | Lowther | A42B 1/24 2/422 |
| 2015/0113708 A1 | * | 4/2015 | Hill | A42B 1/063 2/244 |

\* cited by examiner

DISPOSABLE ABSORBENT VISOR PADS AND METHOD OF USE

FIELD OF INVENTION

The present invention relates to the field of headgear, and more particularly to the field of headgear with visors and means for preventing the dripping of liquid/moisture from such visors.

BACKGROUND OF THE INVENTION

Helmets and hardhats are widely used for head protection in sports and industry. While the benefits of such headgear are evident, they present certain problems when impinged by liquids and/or moisture, such as during a rainstorm or an incident involving the release of a liquid or spray. Liquid or moisture droplets falling on the visor of the headgear are not retained there, but rather drip off the edge of the visor into the face and vision field of the wearer. These dripping liquid droplets are annoying and tend to distract the wearer from the task at hand, impairing the wearer's efficiency and causing safety hazards.

One way to address this problem would be to incorporate a permanent outer absorbent layer in the upper surface of the visor, but such a permanent appendage lacks utility during dry conditions, and its absorbency will degrade over time, requiring uneconomical replacement of the entire headgear. The present invention offers a better solution by providing disposable absorbent pads that can be temporarily attached to a visor during rainy/damp conditions and then removed when no longer needed.

SUMMARY OF THE INVENTION

The present invention comprises a disposable absorbent pad, which is removably attachable to the upper surface of the visor of a headgear. It should be noted that, as used herein, the terms "headgear" and "visor" are not limiting, but refer, respectively, to any type of hat, cap, helmet or other head covering, and to any type of visor, bill, eye-shade or brim associated with such headgear.

The disposable absorbent pad has an obverse side, conforming to the shape, size and area of the visor's upper surface. The obverse side of the disposable absorbent pad consists of a flexible layer of a moisture-absorbent material. Advantageously, the absorbency of this material is such that it can sustain a prolonged drenching without becoming saturated. One material which has been found suitable for this purpose is sold under the tradename "PIG Grippy Adhesive Floor Mat"™, manufactured by New Pig Corporation. It should be understood, however, that many other suitable absorbent materials, well known to those skilled in the art, can be used in the present invention. The obverse side of the disposable absorbent pad can be made in a variety of colors to match the color of the visor, so as not to be visually obtrusive.

The disposable absorbent pad has a reverse side, congruous with the obverse side, and containing one or more means for attaching the disposable absorbent pad to the upper surface of the visor. As applied to a plastic or metal visor, this attachment means will preferably be a flexible peel-and-stick adhesive layer covering the entire reverse side of the disposable absorbent pad. As applied to a fabric or cardboard visor, the attachment means will preferably consist of multiple cooperating hook-and-loop strips. Alternately, the attachment means can consist of multiple mechanical clips or clamps of the kind well known to those skilled in the art.

The present invention is deployed by selecting a disposable absorbent pad conforming to the size, shape, area, and color of the target visor. The pad's attachment means are then readied by either peeling the protective strip off the adhesive layer or attaching the cooperating strips of the hook-and-loop fasteners to the visor, depending on its surface material. When the rain/dampness has subsided, the pad is removed from the visor and disposed.

The foregoing summarizes the general design features of the present invention. In the following sections, specific embodiments of the present invention will be described in some detail. These specific embodiments are intended to demonstrate the feasibility of implementing the present invention in accordance with the general design features discussed above. Therefore, the detailed descriptions of these embodiments are offered for illustrative and exemplary purposes only, and they are not intended to limit the scope either of the foregoing summary description or of the claims which follow.

DETAILED DESCRIPTION OF THE PREFERRED EMBODIMENTS

Figure 1:
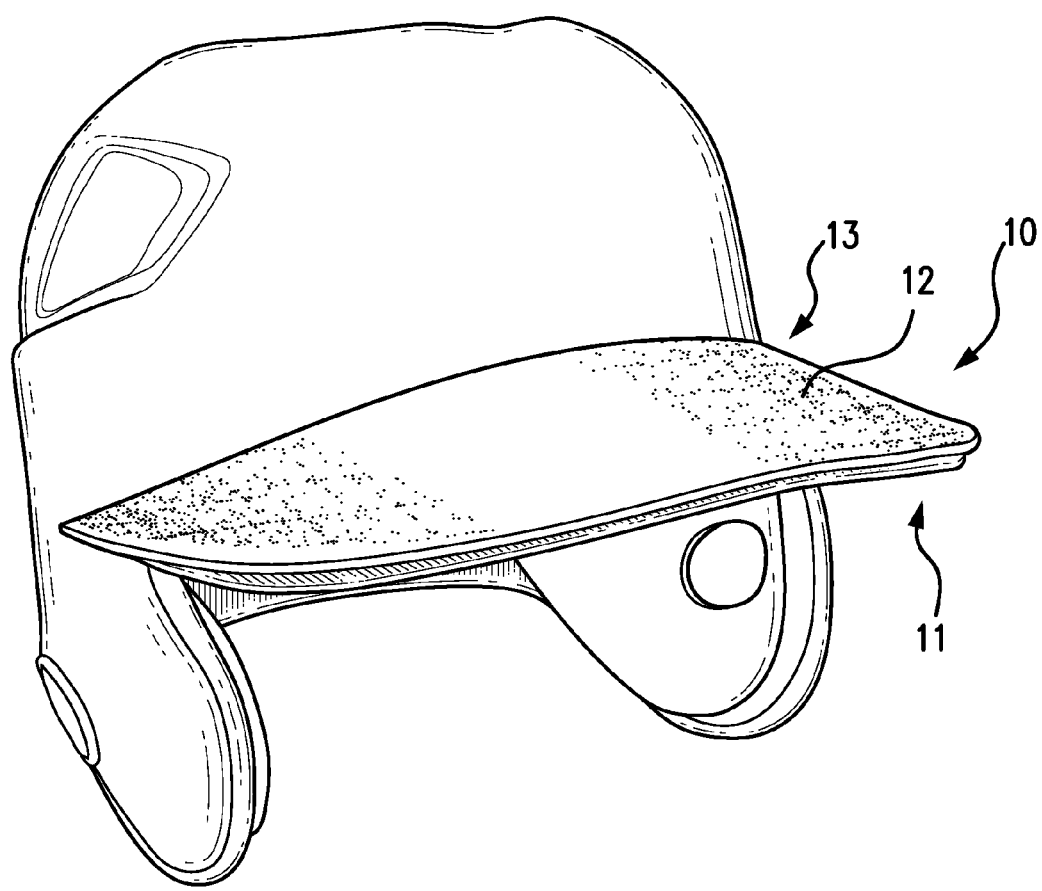
FIG. 1 is a perspective view of an exemplary embodiment of the disposable absorbent pad attached to visor of a baseball batting helmet.

Referring to FIG. 1, an exemplary disposable absorbent pad 10 is shown attached to the visor 11 of a hard plastic baseball helmet. In FIG. 4, another exemplary embodiment of the disposable absorbent pad 10 is shown attached to the visor 11 of a hard hat. The absorbent material 12 is sized and shaped to cover the entire upper surface of the visor 11, so as to maximize its moisture retention capacity. The absorbent material 12 and its adhesive backing 15 (FIG. 3) are also flexible enough to enable the pad 10 to be bent to conform to the curvature of the visor 11.

Figure 2:
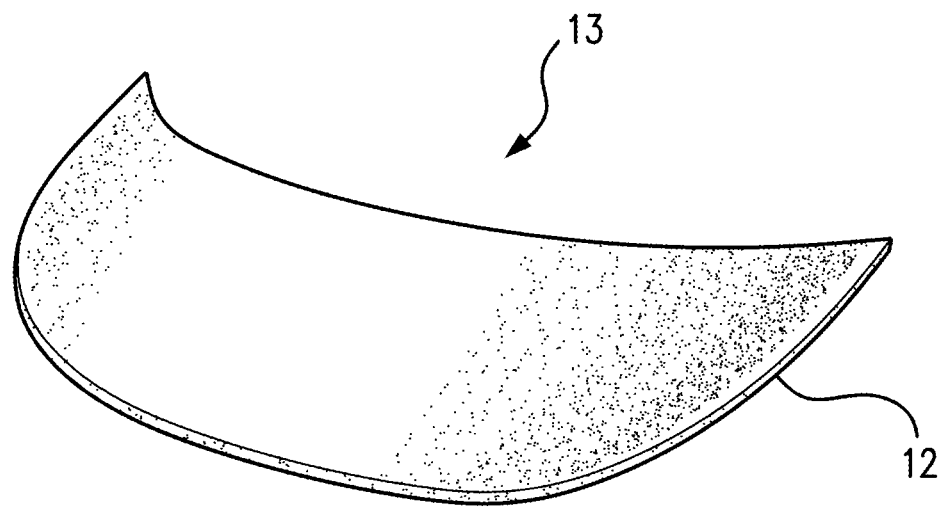
FIG. 2 is a perspective view of the obverse side of an exemplary disposable absorbent pad.
Figure 3:
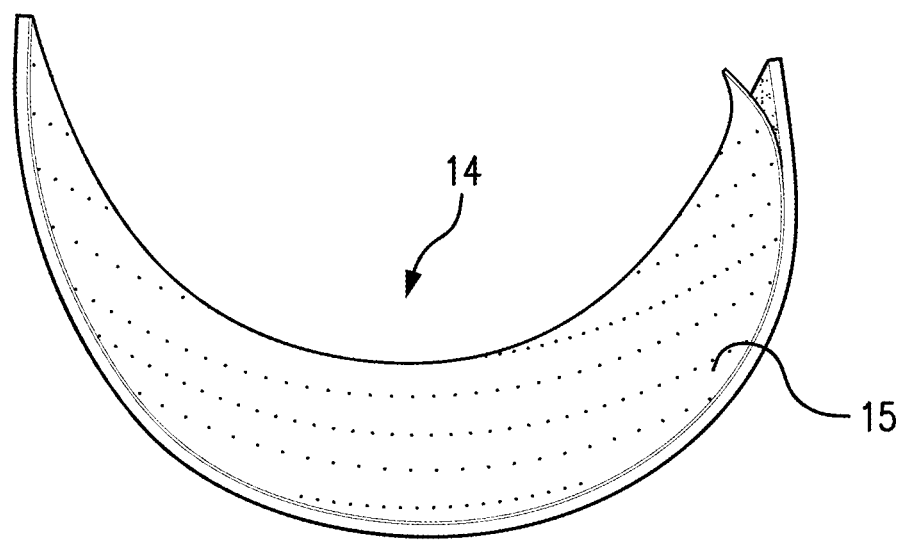
FIG. 3 is a perspective view of the reverse side of an exemplary disposable absorbent pad.
Figure 4:
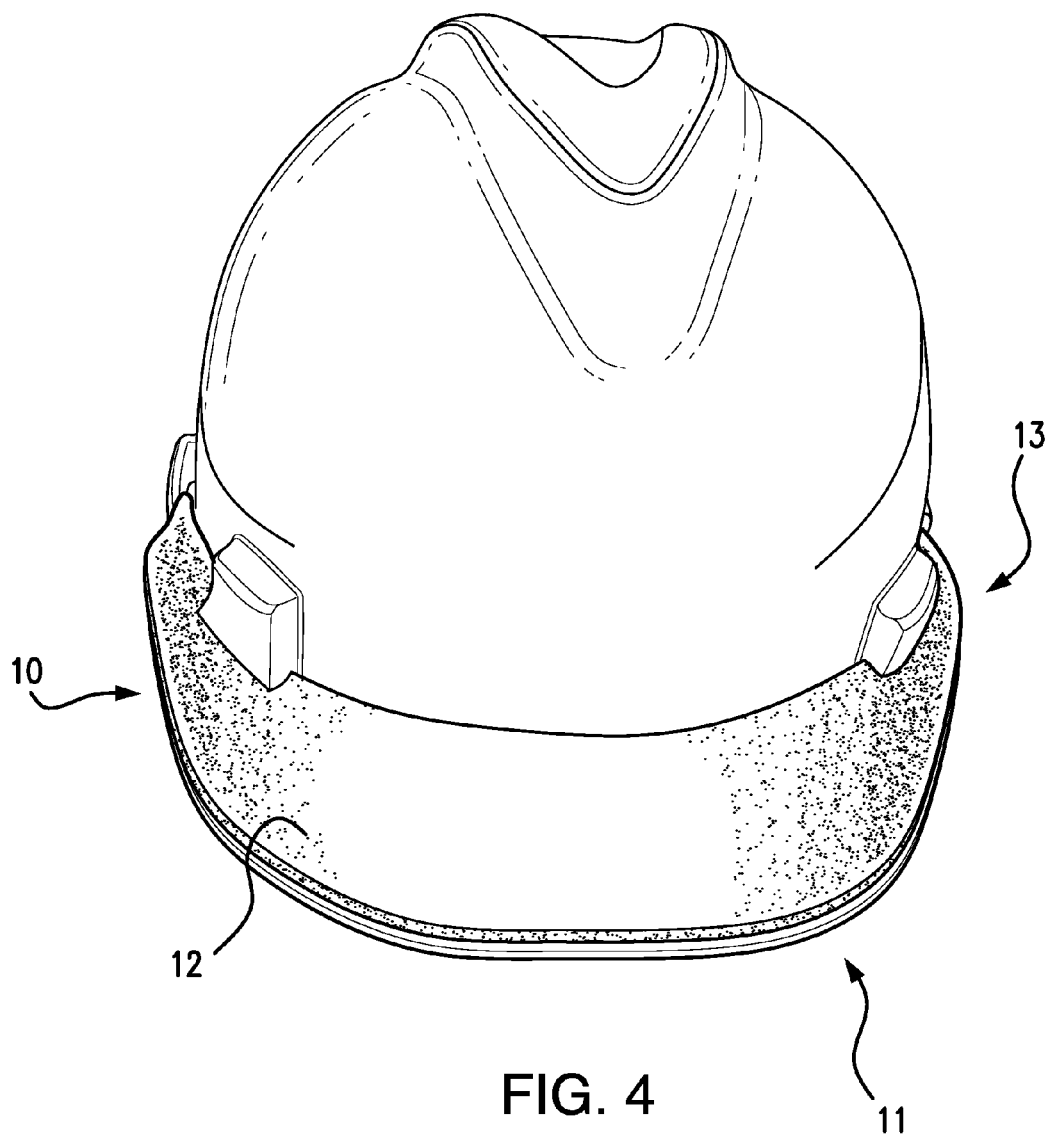
FIG. 4 is a perspective view of an exemplary embodiment of the disposable absorbent pad attached to the visor of a hard hat.

Referring to FIGS. 2 and 3, the obverse side 13 and reverse side 14, respectively, of the pad 10 are depicted. In this particular embodiment, as applied to a hard plastic helmet, the preferred attachment means consists of a peel-and-stick adhesive layer 15, which covers the entire reverse side 14 of the pad 10.

After each use, the pad 10 is disposable and replaceable with another equivalent pad 10. Although the preferred embodiments of the present invention have been disclosed for illustrative purposes, those skilled in the art will appreciate that many additions, modifications and substitutions are possible, without departing from the scope and spirit of the present invention as defined by the accompanying claims.

What is claimed is:

1. A method for preventing drippage of moisture or liquid from an upper surface of a visor of a headgear, comprising the following steps:

(a) providing a disposable absorbent pad, which is removably attachable to the upper surface of the visor;
(b) providing in the disposable absorbent pad an obverse side, conforming in shape, size and area to the upper surface of the visor, and consisting of a flexible layer of a material which absorbs and retains moisture;
(c) providing in the disposable absorbent pad a reverse side, congruous with the obverse side, and comprising one or more visor attachment means for removably attaching the disposable absorbent pad to the visor;
(d) attaching the disposable absorbent pad to the upper surface of the visor when moisture or liquid is impinging upon the visor, so as to prevent such moisture or liquid from dripping off the visor into a field of vision of a wearer of the headgear;
(e) detaching the disposable absorbent pad from the upper surface of the visor when the moisture or liquid is no longer impinging upon the visor; and
(f) disposing of the disposable absorbent pad.

2. The method of claim 1, wherein the visor attachment means consists of a flexible peel-and-stick adhesive layer that is coextensive with the reverse side of the disposable absorbent pad.

3. The method of claim 1, wherein the visor attachment means consists of one or more cooperating hook-and-loop strips.

\* \* \* \* \*